United States Patent [19]

Wallach

[11] Patent Number: 5,234,767

[45] Date of Patent: * Aug. 10, 1993

[54] HYBRID PAUCILAMELLAR LIPID VESICLES

[75] Inventor: Donald F. H. Wallach, Brookline, Mass.

[73] Assignee: Micro-Pak, Inc., Wilmington, Del.

[*] Notice: The portion of the term of this patent subsequent to Mar. 27, 2007 has been disclaimed.

[21] Appl. No.: 759,732

[22] Filed: Sep. 12, 1991

Related U.S. Application Data

[63] Continuation of Ser. No. 410,647, Sep. 21, 1989, abandoned, which is a continuation-in-part of Ser. No. 157,571, Mar. 3, 1988, Pat. No. 4,911,928, which is a continuation-in-part of Ser. No. 25,525, Mar. 13, 1987, abandoned, and a continuation-in-part of Ser. No. 78,658, Jul. 28, 1987, Pat. No. 4,855,090, and a continuation-in-part of Ser. No. 124,824, Nov. 24, 1987, Pat. No. 4,917,951.

[51] Int. Cl.$^5$ .................... A61K 9/127; B01J 13/02
[52] U.S. Cl. .................... 428/402.2; 264/4.1; 424/450; 436/829; 514/818
[58] Field of Search .................... 434/450; 436/829

[56] References Cited

U.S. PATENT DOCUMENTS

| | | | |
|---|---|---|---|
| 3,372,261 | 3/1963 | Leary et al. | 252/DIG. 1 |
| 3,957,971 | 5/1976 | Oleniacz | 424/70 |
| 4,133,874 | 1/1979 | Miller et al. | 428/402.2 X |
| 4,182,330 | 1/1980 | Michaels | 128/260 |
| 4,217,344 | 8/1980 | Vanlerberghe et al. | 424/60 |
| 4,235,871 | 11/1980 | Papahadjopoulos et al. | 424/450 |
| 4,241,046 | 12/1980 | Papahadjopoulos et al. | 424/450 X |
| 4,247,411 | 1/1981 | Vanlerberghe et al. | 264/4.6 |
| 4,348,329 | 9/1982 | Chapman | 260/403 |
| 4,356,167 | 10/1982 | Kelly | 424/450 |
| 4,377,567 | 3/1983 | Geho | 424/1.1 |
| 4,448,765 | 5/1984 | Ash et al. | 424/450 |
| 4,485,054 | 11/1984 | Mezei et al. | 264/4.6 |
| 4,536,324 | 8/1985 | Fujiwara et al. | 252/311 |
| 4,544,545 | 10/1985 | Ryan et al. | 424/1.1 |
| 4,564,599 | 1/1986 | Janoff et al. | 436/507 |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,666,711 | 5/1987 | Vanlerberghe et al. | 424/70 |
| 4,684,625 | 8/1987 | Eppstein et al. | 514/19 |
| 4,692,433 | 9/1987 | Hostetler et al. | 514/12 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,772,471 | 9/1988 | Vanlerberghe et al. | 424/450 |
| 4,789,633 | 12/1988 | Huang et al. | 264/4.1 X |
| 4,855,090 | 8/1989 | Wallach | 264/4.1 |
| 4,911,928 | 3/1990 | Wallach | 424/450 |
| 4,917,951 | 4/1990 | Wallach | 428/402.2 |
| 4,942,038 | 7/1990 | Wallach | 424/450 |

FOREIGN PATENT DOCUMENTS

| | | |
|---|---|---|
| 032578 | 7/1984 | European Pat. Off. |
| 167825 | 6/1985 | European Pat. Off. |
| 3410602 | 9/1984 | Fed. Rep. of Germany |
| 59-106423 | 6/1984 | Japan |
| 61-207324 | 9/1986 | Japan |
| WO8501440 | 4/1985 | PCT Int'l Appl. |
| WO8706499 | 11/1989 | PCT Int'l Appl. |
| 929408 | 6/1963 | United Kingdom |
| 1539625 | 1/1979 | United Kingdom |
| 2078543A | 1/1982 | United Kingdom |
| 2079179A | 1/1982 | United Kingdom |
| 2147263A | 5/1985 | United Kingdom |
| 2198947A | 6/1988 | United Kingdom |

OTHER PUBLICATIONS

L. Stryer: "Biochemistry-Second Edition", W. H. Freeman & Co., New York (1981) pp. 207 and 210.

(List continued on next page.)

*Primary Examiner*—Richard D. Lovering

[57] ABSTRACT

Disclosed are hybrid paucilamellar lipid vesicles containing a phospho- or glycolipid and a nonionic, anionic, or zwitterionic surfactant in the lipid bilayers. The paucilamellar vesicles may have either an aqueous or oil-filled central cavity. A method of manufacture for these vesicles is also disclosed.

20 Claims, No Drawings

OTHER PUBLICATIONS

McCutcheon (Detergents & Emulsifiers, 1973, North American Edition), p. 27.

McCutcheon (Emulsifiers & Detergents, 1982, North American Edition), pp. 26-27.

Ostro (Liposomes, 1983, Marcel Dekker, Inc.), pp. 246-249.

Handjani-Vila et al. (Les niosomes, 1985, pp. 297-313).

Bangham et al., *Diffusion of Univalent Ions Across the Lamallae of Swollen Phospholipids*, J. Mol. Biol. (1965), vol. 13, pp. 238-252.

Gregoriadis, *The Carrier Potential of Liposomes In Biology and Medicine*, New England Journal of Medicine (1976), vol. 295, No. 13, pp. 704-710.

Szoka et al., *Procedure for Preparation of Liposomes With Large Internal Aqueous Space and High Capture by Reverse-Phase Evaporation*, Proc. Natl. Acad. Sciences USA (1978), vol. 9, pp. 4194-4198.

Dousset et al., Methodes de Preparation des Liposomes (1980), pp. 41-72.

Philippot et al., *A Very Mild Method Allowing the Encapsulation of Very High Amounts of Macromolecules into Very Large (1000mm) Unilamellar Liposomes*, Biochimica et Biophysia Acta (1983), vol. 734, pp. 137-143.

Ribier et al., *Bilayer Fluidity of Non-ionic Vesicles, An Investigation by Differential Polarized Phase Fluorometry*, Colloids and Surfaces (1984), vol. 10, pp. 155-161.

Baillie et al., *The Preparation and Properties of Niosomes—Non-ionic Surfactant Vesicles*, J. Pharm. Pharmacol. (1985), vol. 37, pp. 863-868.

Philippot et al., *Extemporaneous Preparation of Large Unilamellar Liposomes*, Biochimica et Biophysia Acta (1985), vol. 821, pp. 79-84.

Puisieux et al., *Problems Technologiques Poses Par L'utilisation des Liposomes Comme Vecteurs de Substances Medicanenteuses*. Encapsulation, Sterilisation, Conservation (1985), pp. 73-113.

Baillie et al., *Non-ionic Surfactant Vesicles, Niosomes, As a Delivery System for the Anti-Leishmanial Drug, Sodium Stibogluconate*, J. Pharm. Pharmacol. (1986), vol. 38, pp. 502-505.

HYBRID PAUCILAMELLAR LIPID VESICLES

REFERENCE TO RELATED APPLICATIONS

This application is a continuation of Ser. No. 410,647, filed Sep. 21, 1989, now abandoned, which is a continuation-in-part of Ser. No. 157,571, filed Mar. 3, 1988, now U.S. Pat. No. 4,911,928, which was a continuation-in-part of Ser. No. 025,525, filed Mar. 13, 1987, now abandoned; said Ser. No. 157,571, filed Mar. 3, 1987, now U.S. Pat. No. 4,911,928, also being a continuation-in-part of Ser. No. 078,658, filed Jul. 28, 1987, now U.S. Pat. No. 4,855,090, and a continuation-in-part of Ser. No. 124,824, filed Nov. 24, 1987, now U.S. Pat. No. 4,917,951.

BACKGROUND OF THE INVENTION

The present invention relates to the production of hybrid paucilamellar lipid vesicles. More particularly, the present invention concerns lipid vesicles which have phospholipids or glycolipids in addition to single-chain non-ionic, anionic, or zwitterionic surfactants as the major components of the walls (or lipid bilayers) of a paucilamellar lipid vesicle.

Lipid vesicles are substantially spherical structures made of materials having a high lipid content, e.g., surfactants or phospholipids. The lipids of these spherical vesicles are organized in the form of lipid bilayers. The lipid bilayers encapsulate an aqueous volume which is either interspersed between multiple onion-like shells of lipid bilayers (forming multilamellar lipid vesicles or "MLV") or the aqueous volume is contained within an amorphous central cavity. The most commonly known lipid vesicles having an amorphous central cavity filled with aqueous medium are the unilamellar lipid vesicles. Large unilamellar vesicles ("LUV") generally have a diameter greater than about 1 $\mu$ while small unilamellar lipid vesicles ("SUV") generally have a diameter of less than 0.2 $\mu$. Lipid vesicles have a variety of uses including adjuvants or carriers for a broad spectrum of materials.

Although substantially all the investigation of lipid vesicles in recent years has centered on multilamellar and the two types of unilamellar lipid vesicles, a fourth type of lipid vesicle, the pauoilamellar lipid vesicle ("PLV"), exists. See Callo and McGrath, Cryobiology 1985, 22(3), pp. 251-267. This lipid vesicle has barely been studied until recently and had only been manufactured with phospholipids surrounding an amorphous aqueous-filled volume. PLV's consist of about 2 to 10 peripheral bilayers surrounding a large, unstructured central cavity. In all PLV's described previous to U.S. patent application Ser. No. 157,571, now U.S. Pat. No. 4,911,928 the disclosure of which is incorporated herein by reference, this central cavity was filled with an aqueous solution. The cited application first disclosed oil-filled vesicles.

Each type of lipid vesicle appears to have certain uses for which it is best adapted. For example, MLV's have a higher lipid content then any of the other lipid vesicles, so to the extent that a lipid vesicle can encapsulate or carry a lipophilic material in the bilayers without degradation, MLV's have been deemed the most advantageous for carrying lipophilic materials. In contrast, the amount of water encapsulated in the aqueous shells between the lipid bilayers of the MLV's is much smaller than the water which can be encapsulated in the central cavity of LUV's, so LUV's have been considered advantageous in transport of aqueous material. However, LUV's, because of their single lipid bilayer structure, are not as physically durable as MLV's and are more subject to enzymatic degradation. SUV's have neither the lipid or aqueous volumes of the MLV's or LUV's but because of their small size have easiest access to cells in tissues.

PLV's, which can be considered a sub-class of the MLV's, possess features of both MLV's and LUV's. PLV's appear to have advantages as transport vehicles for many uses as compared with the other types of lipid vesicles. In particular, because of the large unstructured central cavity, PLV's are easily adaptable for transport of large quantities of aqueous- or oil-based materials. Moreover, the multiple lipid bilayers of the PLV's provides PLV's with additional physical strength and resistance to degradation as compared with the single lipid bilayer of the LUV's. As illustrated in the present application and the previously cited U.S. patent application Ser. No. 157,571, now U.S. Pat. No. 4,911,928 the central cavity of the PLV's can be filled wholly or in part with an apolar oil or wax and then can be used as a vehicle for the transport or storage of hydrophobic materials. The amount of hydrophobic material which can be transported by the PLV's with an apolar core is much greater than can be transported by MLV's.

Conventional methods for producing multilamellar lipid vesicle start by dissolving the lipids, together with any lipophilic additives, in an organic solvent. The organic solvent is then removed by evaporation using heat or by passing a stream of an inert gas (e.g., nitrogen) over the dissolved lipids. The residue is then hydrated with an aqueous phase, generally containing electrolytes and additives such as hydrophilic biologically-active materials, to form multilamellar lipid membrane structures. In some variations, different types of particulate matter or structures have been used during the evaporation process to assist in the formation of the lipid residue. Changing the physical structure of the lipid residue can result in formation of better vesicles upon hydration. Two recent review publications, Gregoriadis, G., ed. *Liposome Technology* (CRC, Boca Raton, Fla.), Vols. 1-3 (1984), and Dousset and Douste-Blazy (in *Les Liposomes*, Puisieux and Delattre, Editors, Techniques et Documentation Lavoisier, Paris, pp.41-73 (1985)), summarize the methods which have been used to make MLV's.

No matter how the MLV's or PLV's are formed, once made it is necessary to determine the effectiveness of the process. Two measurements commonly used to determine the effectiveness of encapsulation of materials in lipid vesicles are the encapsulated mass and captured volume. The encapsulated mass is the mass of the substance encapsulated per unit mass of the lipid and is often given as a percentage. The captured volume is defined as the amount of the aqueous phase trapped inside the vesicle divided by the amount of lipid in the vesicle structure, normally given in ml liquid/g lipid.

Phospholipid vesicles, while mimicking membrane structure because of similarity of materials with naturally occurring membranes, have a number of problems. First, isolated phospholipids are subject to degradation by a large variety of enzymes. Second, the most easily available phospholipids are those from natural sources, e.g., egg yolk lecithin, which contain polyunsaturated acyl chains that are subject to autocatalyzed peroxidation. When peroxidation occurs, the lipid structure breaks down, causing fracture of the lipid vesicle and premature release of any encapsulated material. While hydrogenation may be used to saturate the chains, it is an expensive process which raises the already high cost of the phospholipid starting materials, as well as changing the vesicle stability.

Because of these problems with using plain phospholipids, certain companies, primarily L'Oreal and Micro Vesicular Systems, have been using non-ionic surfactants to form the structure of vesicles. L'Oreal uses primarily polyglycols, e.g., U.S. patent Ser. Nos. 4,772,471 and 4,217,344, while Micro Vesicular Systems has been using primarily polyoxyethylene fatty acid ethers and esters (see U.S. patent application Ser. No. 157,571 now U.S. Pat. No. 4,911,928 and U.S. Pat. No. 4,855,090). The L'Oreal vesicles appear to be classic MLV's while the Micro Vesicular Systems vesicles are primarily PLV's.

For certain uses, e.g., transportation of vesicles through membranes or permeation of the skin, the presence of a small amount of phospholipid and/or glycolipid to the bilayer structure of the vesicles may be important. A problem with using the phospholipids or glycolipids in conjunction with many synthetic surfactants is that most of the surfactants have a non-ionic head group linked to a single hydrophobic chain while most phospholipids and glycolipids have two hydrophobic chains linked to an ionic head group. Use of both single and multiple chain molecules in the structure of vesicle walls may lead to problems in the packing of the lipids which form the lipid bilayers. Under most circumstances, one would expect that any attempt to form a stable vesicle by blending single and multiple chain lipids, particularly when one is a non-ionic lipid while the other is an ionic or zwitterionic lipid, would be difficult at best. In addition, the phospholipids are still subject to phospholipases after vesicle formation. However, the hybrid vesicles are exactly what is needed to solve certain problems of cross-membrane transport, stability and cost.

Accordingly, an object of the invention is to provide stable hybrid lipid vesicles having a non-ionic, zwitterionic, or anionic surfactant and a phospholipid or glycolipid in the lipid bilayers of the vesicles.

A further object of the invention is to provide stable hybrid paucilamellar lipid vesicles encapsulating a water-immiscible material within the central amorphous cavities of the vesicles.

Another object of the invention is to provide a method of manufacture of hybrid vesicles.

A still further object of the invention is to provide a vehicle for the transport of oil-soluble or water-soluble materials into the skin.

These and other objects and features of the invention will be apparent from the following description.

SUMMARY OF THE INVENTION

The present invention features hybrid paucilamellar lipid vesicles having phospholipids or glycolipids in addition to single-chain non-ionic, anionic, or zwitterionic non-phospholipids in the lipid bilayers. These hybrid vesicles are particularly useful for transport of oil-soluble or water-soluble material into the skin.

The hybrid paucilamellar lipid vesicles having phospholipids or glycolipids in addition to non-ionic or zwitterionic surfactants in their lipid bilayers consist of 2-10 lipid bilayers arranged in the form of substantially spherical shells separated by aqueous layers surrounding a large amorphous central cavity free of lipid bilayers. The lipid bilayers have about 0-30% phospholipids and/or glycolipid and 0-75% single-chain non-ionic, anionic, or zwitterionic surfactant, preferably with other materials such as 0-25% of a sterol and 0-5% of a charge-producing agent. The preferred non-ionic surfactants are selected from the group consisting of polyoxyethylene fatty ethers having the formula

$$R_1\text{---}CO(C_2H_4O)_n H$$

where $R_1$ is lauric, myristic, or palmitic acid or their derivatives, single or double unsaturated octadecyl acids or their derivatives, or double unsaturated eicodienoic acids or their derivatives and n ranges from 2-4;

diethanolamides having the formula

$$(HOCH_2\text{---}CH_2)_2 NCO\text{---}R_2$$

where $R_2$ is caprylic, lauric, myristic, palmitic, stearic, or linoleic acid or their derivatives;

polyoxyethylene fatty acid esters having the formula

$$R_3\text{---}COO(C_2H_4O)_m H$$

where $R_3$ is lauric, myristic, palmitic, stearic, or oleic acids or their derivatives, double unsaturated octadecyl acids or their derivatives, or double unsaturated eicodienoic acids or their derivatives and m ranges from 2-4;

long chain acyl hexosamides having the formula

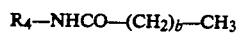
$$R_4\text{---}NHCO\text{---}(CH_2)_b\text{---}CH_3$$

where b ranges from 10-18 and $R_4$ is a sugar molecule selected from a group consisting of glucosamine, galactosamine, and N-methylglucamine;

long chain acyl amino acid amides having the formula

$$R_5\text{---}CHCOOH\text{---}NHCO\text{---}(CH_2)_c\text{---}CH_3$$

where c ranges from 10-18 and $R_5$ is an amino acid side chain;

long chain acyl amides having the formula

$$HOOC\text{---}(CH_2)_d\text{---}N(CH_3)_2\text{---}(CH_2)_3\text{---}NCO\text{---}R_6$$

where $R_6$ is an acyl chain having 12-20 carbons and not more than two unsaturations, and d ranges from 1-3;

polyoxyethylene (20) sorbitan mono- or trioleate;

polyoxyethylene glyceryl monostearate with 1-10 polyoxyethylene groups;

glycerol monostearate;

sarcosinamides having the formula

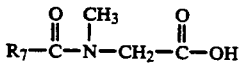

where $R_7$ is selected from the group consisting of single-chain carbonyl derivatives of $C_{12}$-$C_{20}$ fatty acids; and betaines having the formula

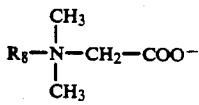

where $R_8$ is selected from the group consisting of long-chain fatty acid esters, most Preferably oleoyl propyl betaine having the formula

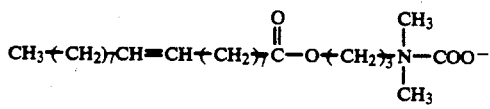

Phospholipids and/or glycolipids particularly useful in the invention include phosphatidylcholines, phosphatidylethanolamines, phosphatidylserines, inositolphosphatides, sphingomyelins, ceramides, cerebrosides, gangliosides, sulfatides, and mixtures and derivatives thereof. Phospholipids or glycolipids with saturated hydrocarbon chain length greater than sixteen are not as useful as smaller chain or unsaturated chain molecules in the invention because they lack some chain fluidity. If a charge-producing agent is used, preferred charge-producing agents include dicetyl phosphate, quaternary ammonium salts, cetyl sulfate, sarcosinamides, phosphatidic acid, phosphatidyl serine, and fatty acids such as oleic acid or palmitic acid.

The preferred hybrid paucilamellar vesicles of the invention have a central cavity carrying either water-soluble materials or water-immiscible oily-solution, preferably selected from a group consisting of oils, waxes, natural and synthetic triglycerides, acyl ethers, petroleum derivatives and their analogues and derivatives, encapsulated within the central amorphous cavity. This type of water-immiscible material can act as a carrier for materials which are not soluble in an aqueous phase. In addition, it may also be used for materials which are not dissolvable or soluble in the lipids which form the bilayers. If the water-immiscible oil, such as a peanut oil, tristearin or mineral oil is used, the amount of non-ionic or zwitterionic surfactant which is needed to form stable vesicles is decreased. In fact, under certain circumstances, oil-filled paucilamellar vesicles may be formed using the methods of the invention without the addition of any non-ionic or zwitterionic surfactant. However, the most stable hybrid vesicles appear to be formed with 10-30% phospholipid and/or glycolipid, 5-20% of a sterol which is cholesterol, about 1% of a charge-producing agent such as oleic acid, and the remainder constituting the surfactant.

The invention further features a method of producing the hybrid vesicles of the invention. The phospholipid and/or glycolipid and non-ionic or zwitterionic surfactant are blended, with heating if necessary, until a homogeneous lipid layer is formed. If a water-immiscible oil is to be encapsulated, it is blended in the already formed lipid phase, forming a lipophilic phase. If any oil-soluble or oil-suspendable materials are to be encapsulated within the paucilamellar vesicles, they are first dispersed in the oil. The term "dispersed" as used herein includes dissolution or forming a suspension or colloid to yield a flowable phase. If no oil is used, the lipid phase is the lipophilic phase.

Once a lipophilic phase is made, it is blended with an aqueous phase under shear mixing conditions to form the vesicles. "Shear mixing" is defined as the mixing of the lipophilic phase with the aqueous phase under turbulent or shear conditions which provide adequate mixing to hydrate the lipid and form lipid vesicles. Shear mixing achieved by liquid shear which is substantially equivalent to a relative flow rate for the combined phases of about 5-30 m/s to a 1 mm orifice. The use of shear mixing conditions disrupts any lamellae which may form so that the vesicles are formed without the formation of a separable lamellar phase.

The same materials which have been previously described for the vesicles are useful in the methods of the invention. Briefly, the formed lipophilic phase is shear mixed with an excess of aqueous, e.g., 10:1:aqueous:-lipid, and the resulting vesicles, which form in under a second, are then separated and can be used any of a variety of other uses.

The following description will further explain the invention.

DETAILED DESCRIPTION OF THE INVENTION

The hybrid vesicles of the invention can be used for a variety of purposes, including the function of a carrier for transport of materials across membranes or skin that would otherwise not be transportable. In fact, the vesicles of the invention could be used for any purpose where lipid vesicles such as liposomes are now being used or contemplated. These lipid vesicles are characterized by 2-10 lipid bilayers or shells with small aqueous volumes separating each substantially spherical lipid shell. The innermost lipid bilayer surrounds a large, substantially amorphous central cavity which may be filled with either an aqueous solution or a water-immiscible oil. This central cavity acts as a "cargo hold," allowing delivery of a variety of materials to the desired location.

For certain uses, the incorporation of a charge producing amphiphile, yielding a net positive or negative charge to the lipid vesicles, is helpful. The preferred negative charge producing materials are carboxylic acids such as oleic and palmitic acids, dicetyl phosphate, cetyl sulphate, sacrosinamides, phosphatidic acid, phosphatidyl serine, and mixtures thereof. In order to provide a net positive charge to the vesicles, long chain amines, e.g., stearyl amines or oleyl amines, cationic local anaesthetics such as lidocaine, long chain pyridinium compounds, e.g., cetyl pyridinium chloride, quaternary ammonium compounds, or mixtures of these can be used.

The vesicles may also include targeting molecules, either hydrophilic or amphiphilic, which can be used to direct the vesicles to a particular target in order to allow release of the material encapsulated in the vesicle at a specified biological location. If hydrophilic targeting molecules are used, they can be coupled directly or via a spacer to a residue of the polar portion of the surfactant, or they can be coupled, using state of the art procedures, to molecules such as palmitic acid, long chain amines, or phosphatidyl ethanolamine. If spacers are used, the targeting molecules can be interdigitated into the hydrophilic core of the bilayer membrane via the acyl chains of these compounds. Preferred hydrophilic targeting molecules include monoclonal antibodies, other immunoglobulins, lectins, and peptide hormones.

For certain uses, targeting molecules which were linked to the lipid bilayers themselves, through the use of a sulfhydryl bond, are preferred. U.S. patent application Ser. No. 320,944 describes a linkage of this type which yields high efficiency targeting. Molecules containing sulfhydryl groups are incorporated into the structure of the bilayers and a bifunctional cross-linking reagent is used to link the targeting molecule to the bilayers.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Preferred amphiphilic targeting molecules are neutral glycolipids, galactocerebrosides (e.g., for hepatic galactosyl receptors), or charged glycolipids such as gangliosides.

Vesicles made using the methods of the present invention can be used in diagnostic testing, e.g., agglutination testing of immunological systems. The vesicles can also be used as markers or labels for visualization, e.g., swelling or shrinking in the presence of an immune reaction, or for radiography or NMR.

Hydrophilic materials which can be encapsulated include minerals such as titanium dioxide and silicas, viruses, macromolecules, immunological adjuvants such as muramyl dipeptide, peptide hormones such as insulin, calcitonin and glucagon, hypothalmic peptides, pituitary hormones, growth factors such as angiogenic, epithelial and epidermal growth factors, lymphokines such as interleukin-2 and interferon, blood proteins such as hemoglobin and Factor VIII, water-soluble plant hormones and pesticides, radionucleotides, contrast materials for radiological and NMR diagnosis, cancer cytostatics, and antibiotics. Examples of lipophilic materials which can be encapsulated include steroid hormones, pheromones, porphyrins, organic pesticides, fungicides, insect repellents, lipophilic vitamins and derivatives, alkyds, epoxy polyurethanes, fluorocarbons, and related resins. Oil based materials include an exclusive listing of additional lipophilic materials and materials which form colloids or suspensions in oil. A more complete listing of the types of pharmaceuticals that could be encapsulated in lipid vesicles is included in Gregoriadis, G., ed. *Liposome Technology* (CRC, Boca Raton, Fla.), Vols. 1-3 (1984).

The paucilamellar lipid vesicles can be made by a variety of devices which provides sufficiently high shear for shear mixing. There are a large variety of these devices available on the market including a microfluidizer such as is made by Biotechnology Development Corporation, a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the lipid vesicles of the present invention.

A device which is particularly useful for making the lipid vesicles of the present invention has been developed by Micro Vesicular Systems, Inc., Vineland, N.J. and is further described in U.S. patent application Ser. No. 163,806, filed May 3, 1988, now U.S. Pat. No. 4,895,452. Briefly, this device has a substantially cylindrical mixing chamber with at least one tangentially located inlet orifice. One or more orifices lead to a reservoir for the lipophilic phase, mixed with an oil phase if lipid-core PLV's are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., less than 1 second, and are removed from the chamber through an axially located discharge orifice. In a preferred embodiment, there are four tangentially located inlet orifices and the lipid and aqueous phases are drawn from reservoirs, through positive displacement pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. As noted, in most circumstances, turbulent flow is selected to provide adequate mixing.

For small scale, e.g., experimental uses, shear mixing may be carried out using merely a series of syringes and a stopcock joining them. This "syringe method" uses one syringe containing the lipophilic phase, heated if necessary for flowability, which is then linked, via a stopcock, to a second, larger syringe containing an excess of an aqueous phase. The lipid and aqueous phase are then blended rapidly through the stopcock for a short time, e.g, normally less than a minute. This blending causes sufficient shearing to form the paucilamellar vesicles of the invention without the formation of an intermediate or separate lamellar phase. In fact, the formation of a separable lamellar phase would so clog or disrupt the flow as to make this method impossible to use.

When the water-immiscible oil is used, the oil displaces a portion of the aqueous phase as the vesicles are formed. The oil stabilizes the vesicles, leading to high fracture strength and longer term stability than vesicles made without oil. Although it is not necessary for understanding the invention, it is theorized that a very small amount of the surfactant acts as a stabilizing agent, stabilizing the boundary between the aqueous volume and the oil volume, allowing the oil droplet to form. In fact, the oil-filled vesicles are so stable that paucilamellar oil-filled vesicles can be formed from phospholipids using the methods of the invention without the addition of any non-ionic or zwitterionic surfactant, while aqueous-filled vesicles cannot be formed using the same materials and methods.

The following Examples will more clearly illustrate and delineate the scope of the present invention.

EXAMPLE 1

In this invention, egg yolk phosphatidylcholine (Lipoid 100, Lipoid ViCt, Ludwigshafen, GFR), was used in conjunction with a polyoxyethylene ether surfactant to form stable aqueous-based vesicles. These vesicles show high lipid uptake per/g of lipid and small size.

Table I lists the ingredients used to make the vesicles of this Example.

TABLE 1

| | |
|---|---|
| Egg Yolk Phosphatidylcholine | 1.00 g |
| Polyoxyethylene-2 Cetyl Ether (Brij 52) | 1.00 g |
| Cholesterol | 0.25 g |

TABLE 1-continued

| | |
|---|---|
| Oleic Acid | 0.02 g |

Briefly, approximately 1 g of egg yolk phosphatidylcholine was blended with 1 g of polyoxyethyiene-2 cetyl ether (Brij 52, ICI Americas, Inc.), 0.25 g cholesterol (Sigma Chemical Co.) and 0.02 g oleic acid (J. T. Baker) as a charge-producing agent at approximately 65° C. A homogeneous lipid phase was obtained. One ml of the lipid phase was then shear mixed with 9 ml of phosphate buffered saline for approximately 2 minutes using a syringe method as described below.

The lipophilic phase is placed in a 10 ml syringe and is attached through a stopcock having about a 1 mm orifice to a 25 ml syringe which contains the aqueous phase, phosphate buffered saline. After the injection of the lipid phase into the aqueous phase, a second 25 ml syringe replaces the 10 ml syringe and the solution is rapidly forced through the stopcock from one syringe to the other. The resulting vesicles form in less than 1 minute.

The milky suspension which was obtained by the syringe method was combined with 20% dextran in saline at a centrifuge of 3000 rpm's for 15 minutes in a Beckman GP centrifuge. A liposomal layer separated at the top of the centrifuge tube.

Microscopic examination showed spherical paucilamellar lipid vesicles which were not distinguishable from vesicles which did not have the phosphatidylcholine. The mean particle diameter was approximately 0.171 % and the volume uptake was approximately 7.2 ml of phosphate buffered saline/g lipid.

EXAMPLE 2

This Example illustrates the oil-based paucilamellar vesicles of the invention. A lipid phase identical to that described in Example 1 was manufactured. One ml of that lipid phase was then blended with 1 ml of mineral oil (Drakeol 19), forming a lipophilic phase. The resulting 2 ml of the lipophilic phase was then blended with 9 ml of phosphate buffered saline using the syringe technique as described above.

Again, a milky solution is obtained which upon dextran centrifugation yields oil-filled paucilamellar vesicles. All of the oil is encapsulated within the vesicles, which also have a volume uptake of approximately 3 ml of the phosphate buffered saline/g lipid (excluding the mineral oil). The mean particle diameter was approximately 0.654 $\mu$.

EXAMPLE 3

This Example illustrates that the methods of the invention may be used to form phospholipid paucilamellar oil-filled vesicles. Table 2 gives the ingredients used.

TABLE 2

| | |
|---|---|
| Egg Yolk Phosphatidylcholine | 1.00 g |
| Cholesterol | 0.20 g |
| Oleic Acid | 0.02 g |
| Mineral Oil (Drakeol 19) | 1 ml |

One g of egg yolk phosphatidylcholine was blended with 0.2 g cholesterol and 0.02 g oleic acid by heating to 65°. This lipid phase was then blended with 1 g mineral oil (Drakeol 19) to form a lipophilic phase. Approximately 2 ml of lipophilic phase was then blended, using the syringe technique as previously described, with 4 ml of phosphate buffered saline. The resulting milky suspension was separated on a 20% dextran and saline gradient using centrifugation of 3,000 rpm for 15 minutes. A 3 ml liposomal layer separated on top of the centrifuge tube.

Microscopic examination showed spherical, oil-filled paucilamellar lipid vesicles. The aqueous volume uptake was approximately 3 ml/g phospholipid.

EXAMPLE 4

This Example and the following Examples (Examples 5-7) illustrate the use of a mixed phospholipid/glycolipid as part of the structure of the paucilamellar vesicles of the invention. Table 3 illustrates the materials used to form the lipid bilayers in this Example.

TABLE 3

| | |
|---|---|
| Type VIII Brain Extract | 0.76 g |
| Polyoxyethylene-5 Oleyl Ether | 1.99 g |
| Cholesterol | 0.58 g |
| Oleic Acid | 0.08 g |

The type VIII brain extract, which is 30% sphingomyelin (a phospholipid), 30% cerebroside (a glycolipid), 10% sulfatide, and the balance other brain lipids is blended with polyoxyethylene-5 oleyl ether, cholesterol and oleic acid at approximately 65° C. to form a lipid phase. Approximately 1 ml of this lipid phase was mixed with 9 ml of phosphate buffered saline using the previously described syringe technique. Upon dextran centrifugation, spherical lipid vesicles encapsulating an aqueous phase could be seen under a microscope. The mean particle diameter was approximately 0.21 $\mu$ and the volume uptake was approximately 2.7 ml saline/g lipid.

EXAMPLE 5

In this Example, the mixed brain extract of Example 4 was used to make oil-centered vesicles. The lipid phase was made as described in Example 4 and 1 ml of the lipid phase was combined with an equal volume of peanut oil. The resulting mixture was made into vesicles using the same syringe technique described in Example 4. After dextran centrifugation, vesicles were separated which had a mean diameter of 1.66 microns and a volume uptake of 3.5 ml liquid/g lipid.

Surprisingly, use of mineral oil in place of the peanut oil would not produce vesicles.

EXAMPLE 6

In this Example and the following Example, the same brain extract as was used in Examples 4 and 5 is used to make vesicles, except an entirely different type of surfactant, diethanolamine linoleamide, was added.

Table 4 shows the lipids used in the manufacture of the lipid phase of this Example.

TABLE 4

| | |
|---|---|
| Type VIII Brain Extract | 0.76 g |
| Diethanolamine Linoleamide | 1.78 g |
| Cholesterol | 0.85 g |
| Oleic Acid | 0.10 g |

Approximately 0.76 g of the type VIII brain extract was blended with 1.78 g of diethanolamine linoleamide, 0.85 g cholesterol and 0.10 g oleic acid at 65° C. One ml of this lipid phase was mixed, using the syringe technique, with 8 ml of phosphate buffered saline. After dextran centrifugation, lipid vesicles were observed, showing a mean particle diameter of approximately 0.263 μ. The volume uptake was 5 ml of saline/g lipid.

EXAMPLE 7

In this Example, the same lipid phase was used as in Example 6 except oil-centered vesicles were made. After the formation of the lipid phase, 1 ml of the lipid phase was blended with 1 ml peanut oil before shear mixing using the syringe technique with 8 ml of the phosphate buffered saline. Upon separation, spherical vesicles with the mean particle diameter of approximately 0.323 μ were observed. The volume uptake was approximately 4.5 ml/g lipid.

As with Example 6, mineral oil would not form vesicles.

As can be seen from the results of these Examples, paucilamellar lipid vesicles having high water or oil uptake can be formed with the materials and methods of the present invention. Other testing has shown that if different methods are used, e.g., the Bangham method for manufacture of lipid vesicles, paucilamellar lipid vesicles are not formed using the same materials but rather classic multilamellar lipid vesicles are formed. These MLV's yield a much lower water uptake as compared with PLV's and they exhibit substantially no oil uptake.

The foregoing description is illustrative only and those skilled in the art may find other materials and methods which accomplish the same results. Such other materials and methods are included within the following claims.

What is claimed is:

1. Hybrid paucilamellar lipid vesicles having both a first lipid and a second lipid as structural materials in the lipid bilayers, said vesicle containing 2-10 lipid bilayers in the form of concentric substantially spherical shells, the innermost of said lipid bilayers enclosing a substantially amorphous central cavity, said vesicle bilayers comprising:

10 to 30% of said first lipid selected from a group consisting of phospholipids, glycolipids, and mixtures thereof; and 49 to 75% of second lipid, said second lipid being a nonphospholipid, nonglycolipid surfactant selected from the group consisting of diethanolamides having the formula $$(HOCH_2-CH_2)_2NCO-R_2$$

where $R_2$ is a residue derived from a carboxylic acid selected from the group consisting of caprylic, lauric, myristic, stearic, and linoleic acid;

long chain acyl hexosamides having the formula $$R_4-NHCO-(CH_2)_b-CH_3$$

where b ranges from 10-18 and $R_4$ is a residue derived from a sugar molecule selected from a group consisting of glucosamine, galactosamine, and N-methylglucamine;

long chain acyl amino acid amides having the formula $$R_5-CHCOOH-NHCO-(CH_2)_c-CH_3$$

where c ranges from 10-18 and $R_5$ is an amino acid side chain;

long chain acyl amides having the formula $$HOOC-(CH_2)_d-N(CH_3)_2-(CH_2)_3-NCO-R_6$$

where $R_6$ is an acyl chain having 12-20 carbons and not more than two unsaturations, and d ranges from 1-3;

glycerol monostearate;

sarcosinamides having the formula $$R_7-\overset{O}{\underset{\|}{C}}-\overset{CH_3}{\underset{|}{N}}-CH_2-\overset{O}{\underset{\|}{C}}-OH$$

where $R_7$ is selected from the group consisting of single-chain carbonyl derivatives of $C_{12}-C_{20}$ fatty acids; and betaines having the formula $$R_8-\overset{CH_3}{\underset{\underset{CH_3}{|}}{\overset{|}{N}}}-CH_2-COO^-$$

where $R_8$ is a residue of a long-chain fatty acid ester.

2. The hybrid vesicles of claim 1 wherein said lipid bilayers further comprise a sterol.

3. The hybrid vesicles of claim 2 wherein said sterol is selected from the group consisting of cholesterol, and hydrocortisone.

4. The hybrid vesicles of claim 2 wherein said lipid bilayers further comprise a charge-producing agent.

5. The hybrid vesicles of claim 4 wherein said charge-producing agent is selected from the group consisting of carboxylic acids, dicetyl phosphate, cetyl sulfate, phosphatidic acid, phosphatidyl serine, quaternary ammonium salts, cationic local anaesthetics, and mixtures thereof.

6. The hybrid vesicles of claim 1 wherein said first lipid is selected from the group consisting of phosphatidylcholines, phosphatidylethanolamines, phosphatidylserines, inositolphosphatides, sphingomyelins, ceramides, cerebrosides, gangliosides, and sulfatides.

7. The hybrid vesicles of claim 1 wherein said vesicles comprises oil-filled paucilamellar lipid vesicles.

8. The hybrid vesicles of claim 7 wherein said amorphous central cavity of said oil-filled paucilamellar vesicles comprises a water-immiscible oil.

9. The hybrid vesicles of claim 8 wherein said water-immiscible oil is selected from the group consisting of oils, waxes, natural and synthetic triglycerides, acyl ethers, and petroleum derivatives.

10. Hybrid paucilamellar lipid vesicles having both a first lipid and a second lipid, as structural materials in lipid bilayers, said vesicle containing 2-10 lipid bilayers in the form of concentric substantially spherical shells, the innermost of said lipid bilayers enclosing a substantially amorphous central cavity, said vesicle bilayers comprising:

10 to 30% of said first lipid selected from a group consisting of phospholipids, glycolipids, and mixtures thereof; and 49 to 75% of second lipid, said second lipid being a nonphospholipid, nonglycolipid, surfactant selected from the group consisting of polyoxyethylene fatty acid ethers having the formula $$R_1-CO(C_2H_4O)_nH$$

where $R_1$ is a residue derived from a carboxylic acid selected from the group consisting of lauric, myristic, and palmitic acid, single and double unsaturated octadecyl acids, and double unsaturated eicodienoic acids, and n ranges from 2-10; and

where $R_3$ is a residue derived from a carboxylic acid selected from the group consisting of lauric, myristic, palmitic, stearic, and oleic acids, double unsaturated octadecyl acids, and double unsaturated eicodienoic acids and m ranges from 2-4;

polyoxyethylene (20) sorbitan mono- or trioleate; and polyoxyethylene glyceryl monostearate with 1-10 polyoxyethylene groups.

11. A method of making hybrid paucilamellar lipid vesicles comprising the steps of:

forming a lipid phase by blending a first lipid selected from the group consisting of phospholipids, glycolipids, and mixtures thereof, with a second lipid selected from the group consisting of nonphospholipid, nonglycolipid non-ionic, zwitterionic, and anionic surfactants, and mixtures thereof, and with any other lipophilic molecules to be incorporated into the lipid bilayers of said vesicles;

forming an aqueous phase by blending an aqueous-based solution and any aqueous soluble materials to be incorporated into said vesicles; and shear mixing said lipid phase and said aqueous phase to form said hybrid vesicles without the formation of a separable lamellar phase.

12. The method of claim 11 wherein said second lipid is selected from the group consisting of diethanolamides having the formula

where $R_2$ is a residue derived from a carboxylic acid selected from the group consisting of caprylic, lauric, hyristic, stearic, and linoleic acid;

long chain acyl hexosamides having the formula

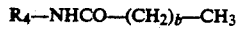

where b ranges from 10-18 and $R_4$ is a residue derived from a sugar molecule selected from a group consisting of glucosamine, galactosamine, and N-methylglucamine;

long chain acyl amino acid amides having the formula

where c ranges from 10-18 and $R_5$ is an amino acid side chain;

long chain acyl amides having the formula

where $R_6$ is an acyl chain having 12-20 carbons and not more than two unsaturations, and d ranges from 1-3;

glycerol monostearate;

sarcosinamides having the formula

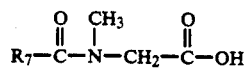

where $R_7$ is selected from the group consisting of single-chain carbonyl derivatives of $C_{12}$-$C_{20}$ fatty acids; and betaines having the formula

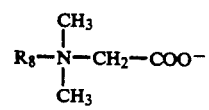

where $R_8$ is a residue of a long-chain fatty acid ester.

13. The method of claim 12 wherein said lipid phase further comprises a sterol.

14. The method of claim 13 wherein said sterol is selected from the group consisting of cholesterol, and hydrocortisone.

15. The method of claim 12 wherein said lipid phase further comprises a charge-producing agent.

16. The method of claim 15 wherein said charge-producing agent is selected from the group consisting of carboxylic acids, dicetyl phosphate, cetyl sulfate, phosphatidic acid, phosphatidyl serine, quaternary ammonium salts, and mixtures thereof.

17. The method of claim 12 wherein said first lipid is selected from the group consisting of phosphatidylcholines, phosphatidylethanolamines, phosphatidylserines, inositolphosphatides, sphingomyelins, ceramides, cerebrosides, gangliosides, and sulfatides.

18. The method of claim 12 wherein said hybrid paucilamellar vesicles are oil-filled hybrid paucilamellar vesicles, said method comprising the further steps of:

forming an oily phase by blending any oil dispersible material to be encapsulated in said vesicles in a water-immiscible oily solution; and blending said lipid phase and said oily phase to form a lipophilic phase both shear mixing with said aqueous phase to form said vesicles.

19. The method of claim 18 wherein said water-immiscible oily solution is selected from the group consisting of oils, waxes, natural and synthetic triglycerides, acyl ethers, and petroleum derivatives.

20. The method of claim 11 wherein said second lipid is selected from the group consisting of polyoxyethylene fatty acid ethers having the formula

where $R_1$ is a residue derived from a carboxylic acid selected from the group consisting of lauric, myristic, and palmitic acid, single and double unsaturated octadecyl acids, and double unsaturated eicodienoic acids, and n ranges from 2-10; and

where $R_3$ is a residue derived from a carboxylic acid selected from the group consisting of lauric, myristic, palmitic, stearic, and oleic acids, double unsaturated octadecyl acids, and unsaturated eicodienoic acids and m ranges from 2-4;

polyoxyethylene (20) sorbitan mono-and trioleate; and polyoxyethylene glyceryl monostearate with 1-10 polyoxyethylene groups.

* * * * *